United States Patent [19]

Kato

[11] Patent Number: 4,671,270

[45] Date of Patent: Jun. 9, 1987

[54] PORTABLE OXYGEN INHALER

[75] Inventor: Yoshimisa Kato, Machida, Japan

[73] Assignee: Midori Anzen Industry Co., Ltd., Tokyo, Japan

[21] Appl. No.: 628,251

[22] Filed: Jul. 6, 1984

[51] Int. Cl.$^4$ ........................ A62B 7/08; A61M 16/00

[52] U.S. Cl. ............................... 128/202.26; 422/120; 422/167

[58] Field of Search ....................... 128/202.26, 201.13; 62/4; 138/114, 149; 55/267; 206/529.1, 529.2, 529.6; 422/120, 122, 125, 126, 305, 167

[56] References Cited

U.S. PATENT DOCUMENTS

| | | | |
|---|---|---|---|
| 2,558,756 | 7/1951 | Jackson et al. | 422/120 |
| 3,536,070 | 10/1970 | Bovard | 128/202.26 |
| 3,580,250 | 5/1971 | Oroza | 128/202.26 |
| 3,607,122 | 9/1971 | Hwoschinsky | 128/202.26 |
| 3,620,683 | 11/1971 | Hwoschinsky et al. | 128/202.26 |
| 3,736,104 | 5/1973 | Churchill et al. | 128/202.26 |
| 3,737,287 | 6/1973 | Churchill et al. | 28/202.26 |
| 3,742,683 | 7/1973 | Sebest et al. | 128/202.26 |
| 3,868,225 | 2/1975 | Tidd | 128/202.26 |
| 3,881,394 | 5/1975 | Netteland | 128/202.26 |
| 3,955,931 | 5/1976 | Thompson | 128/202.26 |
| 3,986,838 | 10/1976 | Reichert | 422/126 |
| 4,066,415 | 1/1978 | Kasama et al. | 422/167 |
| 4,197,213 | 4/1980 | Pietz et al. | 128/202.26 |
| 4,342,725 | 8/1982 | Collins | 128/202.26 |

FOREIGN PATENT DOCUMENTS

| | | | |
|---|---|---|---|
| 673044 | 2/1939 | Fed. Rep. of Germany | 128/202.26 |
| 2243888 | 4/1973 | Fed. Rep. of Germany | 422/167 |
| 201960 | 5/1965 | Sweden | 128/201.13 |
| 2088219 | 6/1982 | United Kingdom | 128/202.26 |

OTHER PUBLICATIONS

Grant, *Hackh's Chemical Dictionary,* 4th Ed. (McGraw Hill Book, Co. 1969), pp. 123–125, 310.

*Primary Examiner*—Henry J. Recla
*Assistant Examiner*—Karin M. Reichle
*Attorney, Agent, or Firm*—George B. Oujevoik

[57] ABSTRACT

A portable oxygen inhaler comprises a chlorate candle, a mask, a tube connecting the chlorate candle and the mask, and a handily-sized case housing these and other component parts as an integral unit. When an actuation pin provided on the chlorate candle is pulled out of the case, oxygen is immediately generated and supplied to the mask.

1 Claim, 5 Drawing Figures

PORTABLE OXYGEN INHALER

BACKGROUND OF THE INVENTION (1) Field of the Invention

This invention relates in general to a portable oxygen inhaler, and more particularly to a portable oxygen inhaler which can be conveniently used as a source of oxygen when someone has difficulty in breathing.

(2) Description of Prior Art

A portable oxygen inhaler using a high-pressure oxygen cylinder is well known. This type of portable oxygen inhaler is large and heavy, and is inconvenient to carry or store. Also since pressurized oxygen is used in such an oxygen inhaler, special care is necessary in the carriage, handling and storage of the inhaler.

OBJECT OF THE INVENTION

An object of the present invention is to provide a portable oxygen inhaler which is small and lightweight, and hence is convenient to carry and store, and with which oxygen can be promptly produced by a very simple operation.

Another object of the present invention is to provide a portable oxygen inhaler which is safe to carry, handle and store.

Still another object of the present invention is to provide a portable oxygen inhaler which requires no inspection during its service life and is easy to maintain.

A further object of the invention is to provide a portable oxygen inhaler which is of a disposable type and which, after disposal, has no ill effects on humans and the environment.

BRIEF DESCRIPTION OF THE DRAWINGS

These and other objects and advantages of the present invention will become more apparent from the following detailed description of the invention, taken in conjunction with the accompanying drawings which schematically illustrate an embodiment of the invention, and in which.

DETAILED DESCRIPTION OF THE INVENTION

The present invention will now be described in detail by way of an embodiment thereof, with reference to the accompanying drawings.

The portable oxygen inhaler according to the present invention comprises a chlorate candle, a mask, a tube connecting the chlorate candle and the mask, and a handily-sized case in which the whole of the device is housed.

Figure 1:
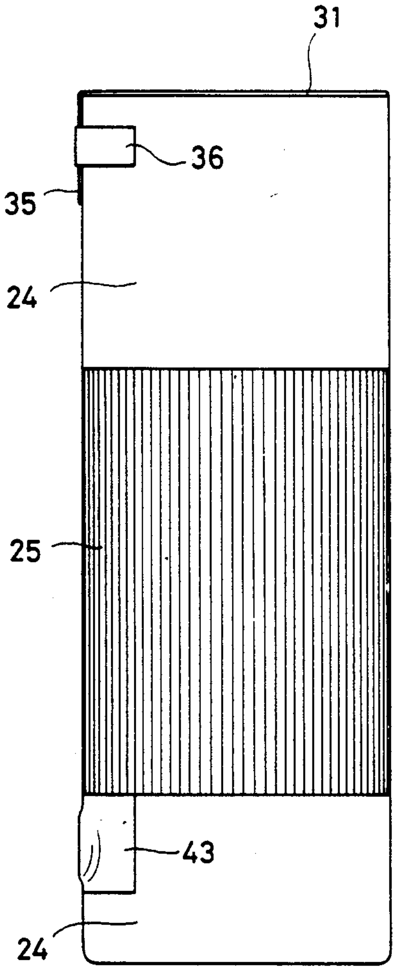
FIG. 1 is a side view of a portable oxygen inhaler according to the present invention.
Figure 2:
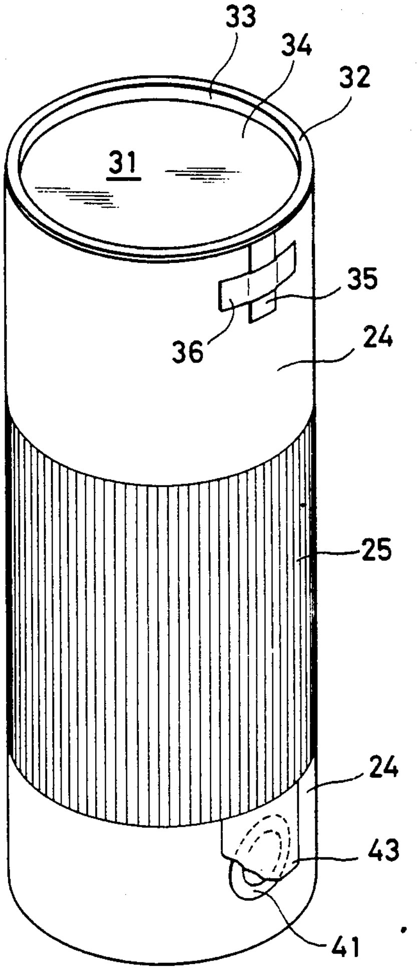
FIG. 2 is a perspective view of the portable oxygen inhaler according to the present invention, with part of the ring seal cut away.
Figure 3:
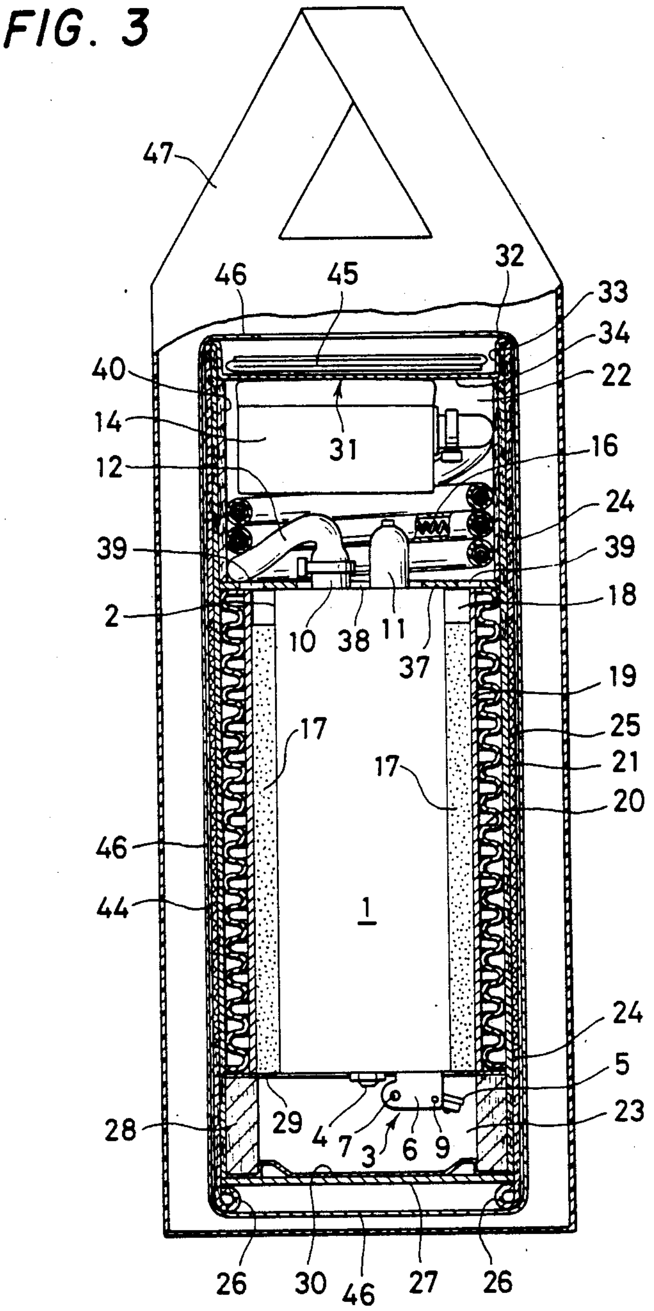
FIG. 3 is a vertical section through the portable oxygen inhaler, when covered with decorative paper and transparent film and placed in a carrier bag.
Figure 4:
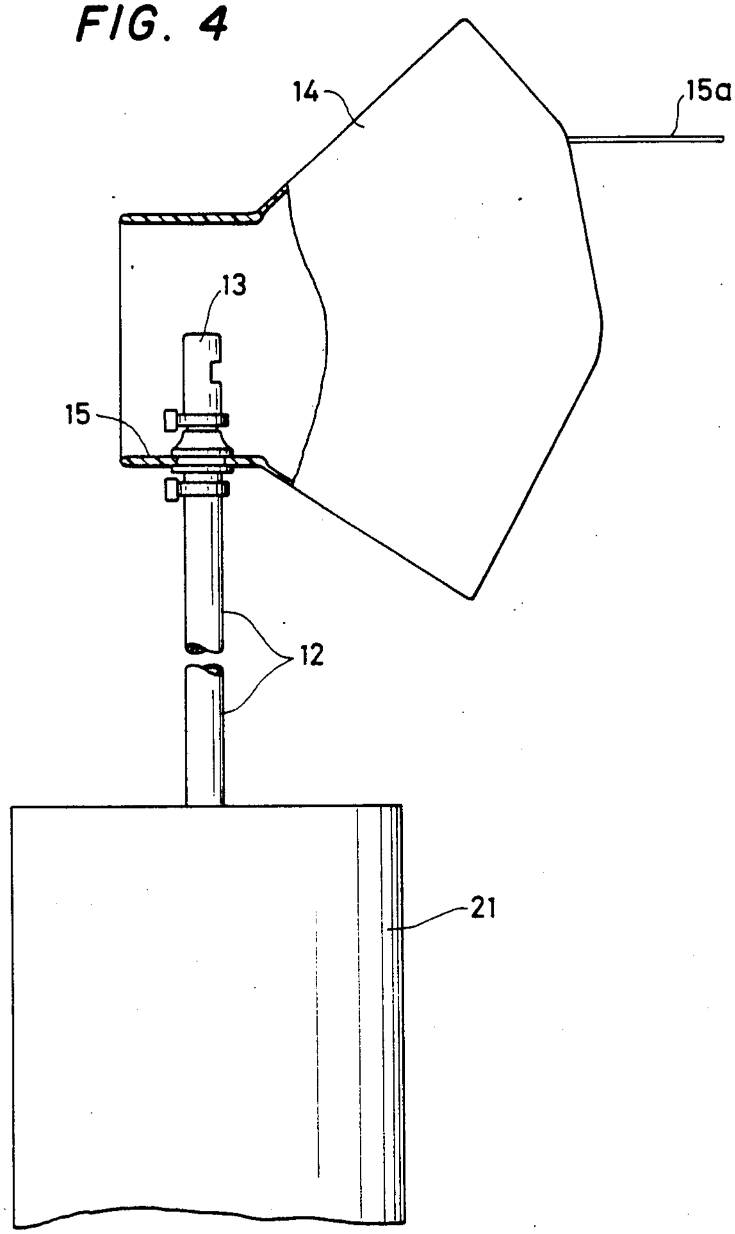
FIG. 4 shows the situation when the mask has been drawn out of the case body, with part of the mask shown in section and part of the case body cut away.
Figure 5:
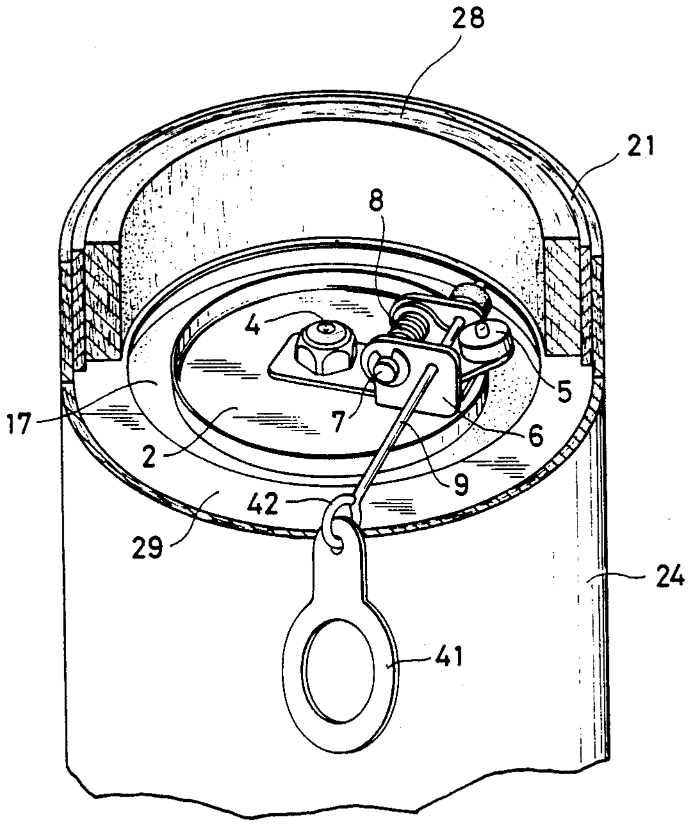
FIG. 5 is a perspective view of the actuator.

Referring to the drawings, numeral 1 designates a chlorate candle consisting of a solid oxygen-generating agent which is mainly composed of a chlorate (hereinafter referred to as the core), with a thermal insulation material wound around the core, this unit is contained in a stainless steel can 2. One end surface of the can 2 is provided with an actuator 3 which, as best shown in FIG. 5, comprises an ignition portion 4 designed to impart initial energy for the reaction of the core and a striker 5 which can strike the ignition portion 4. The striker 5 is pivotally secured by a shaft 7 to a bracket 6 provided close to the ignition portion 4. A spring 8 which biases the striker 5 to rotate and strike the ignition portion 4 is coiled around the shaft 7. One end of the spring 8 is secured to the bracket 6 and the other end is secured to the striker 5. Numeral 9 denotes an actuation pin. When the striker 5 has been rotated against the force of the spring 8 to a position away from the ignition portion 4, the actuation pin 9 is passed through the bracket 6 to hold the striker 5 at that position.

An oxygen outlet 10 and a safety valve 11 are provided at the other end surface of the can 2. One end of a soft plastic or rubber tube 12 is connected to the oxygen outlet 10, and the other end is connected to a normally-closed plug 13. A foldable mask made of a soft, transparent or translucent plastic material is also provided. The plug 13 is inserted into a front opening 15 of the mask. Numeral **15*a* denotes an elastic string attached to the mask 14 which is used for securing the mask over the user's face. A coiled wire 16 is inserted along the full length of the tube 12 to prevent accidental bending of the tube 12 and thus ensure the smooth passage of oxygen therethrough. A thermal insulation cylinder 17 is provided around the chlorate candle 1. This thermal insulation cylinder is made by first covering the can 2 with a cardboard cylinder 19, leaving a space 18 between the cylinder 19 and the outer surface of the can 2, then pouring gypsum into the space 18 so that when it solidifies, it forms the thermal insulation cylinder. An additional thermal insulation layer 20 is provided around the cardboard cylinder 19, it is formed by winding corrugated cardboard around the cardboard cylinder 19**.

Numeral 21 denotes a cardboard case provided around the corrugated cardboard insulation layers 20. The case body 21 is of a size sufficient to leave a space 22 above the chlorate candle 1 for housing the folded mask 14 and tube 12, and a space 23 below the chlorate candle 1 for housing the actuator 3. The case 21 is sheathed with a cover 24 which has a corrugated cardboard portion 25 extending over the part corresponding to the position of the chlorate candle 1. The lower edge of the cardboard cover 24 is curled up, as denoted by numeral 26. The bottom of the case 21 is covered with a cardboard end plate 27 whose peripheral edge is held between the lower end of the case 21 and the curled-up edge 26. An annular block 28 is provided in the space 23, in contact with the inside of the case 21. The annular block 28 is designed to support the chlorate candle 1, the thermal insulation cylinder 17, the cardboard cylinder 19 and the thermal insulation layer 20 on a supporting washer 29. A metallic protective cap 30 is provided attached to the inside of the end plate 27, with the peripheral edge of the cap 30 held between the block 28 and the end plate 27. This protective cap 30 is designed to prevent any denting of the end plate 27 by an external force, to protect the actuator 3. Another metallic cap 31 is provided covering the upper end surface of the case 21. This cap 31 comprises a flange 32 secured to the upper ends of the case 21 and the cover 24, a side wall 33 attached to the inside of the case 21, and a base plate 34. Numeral 35 denotes a tape of which one end is attached to the base plate 34 of the cap 31, and the other end extends out of the case 21 and is fastened to the outer surface of the cover 24 by a seal 36. Numeral 37 denotes a cardboard cover plate provided so as to cover the upper ends of the chlorate candle 1, the thermal insulation cylinder 17, the cardboard cylinder 19 and the thermal insulation layer 20. The center of the cover plate 37 is provided with an a hole 38 through which oxygen outlet 10 and a safety valve 11 passes, and its periphery is provided with a plurality of heat vent holes 30. Numeral 40 denotes a paper cylinder provided in the space 22, attached to the inside of the case 21 so as to support the cap 31. Numeral 41 denotes a pull ring for the actuation pin 9 which is attached to a ring-shaped end 42 of the actuating pin 9 passed through holes (not shown) in the block 28, the case 21 and the cover 24, and which is fastened to the external surface of the cover 24 by a seal 43. Numeral 44 denotes decorative paper covering the entire outer surface of the cover 24. Operating instructions for the oxygen inhaler could be printed on the rear surface of the decorative paper 44. Numeral 45 denotes an instruction manual for the inhaler, the manual being placed in a folded form above the cap 31. Numeral 46 denotes a transparent film covering the whole end surface of the curled-up edge 26, all the decorative paper 44 and the top periphery of the cap 31. Numeral 47 denotes a carrier bag in which the device is placed.

The mode of use and the operation of the portable oxygen inhaler of the present invention with the above structure will be described below. When using the inhaler, the user first tears off the transparent film 46 and the decorative paper 44, then strips off the seal 36 and pulls the tape 35, which removes the cap 31 to open the top end of the case 21. The user then removes the mask 14 and tube 12 folded up in the space 22 and places the mask 14 over the mouth and nose. The user then strips off the seal 43 and, by inserting a finger into and holding the pull ring 41, pulls it to pull the actuation pin 9 out of the bracket 6. The striker 5 is now freed and is rotated to strike the ignition portion 4 by the force stored by the spring 8. This percussion is transmitted to the lower end of the core to initiate its oxygen-generating reaction. This reaction progresses from the lower to the upper end of the core so that oxygen is generated continuously. The generated oxygen passes through the tube 12 and reaches the plug 13 which is normally closed. Since the plug 13 automatically opens with a rise in oxygen pressure, oxygen is supplied to the mask 14 so that the user wearing the mask can inhale the oxygen and maintain normal respiration.

The chlorate candle 1 generates heat simultaneously with the generation of oxygen, which increases the surface temperature of the can 2. In the inhaler of the present invention, however, the outer surface of the can 2 is surrounded with a thermal insulation cylinder 17 which is composed of gypsum (calcium sulfate, $CaSO_4.2H_2O$) which, when heated to 128° C., is converted into plaster of Paris ($CaSO_4.\frac{1}{2}H_2O$) and, at 163° C., is further converted into calcium sulfate anhydride ($CaSO_4$), so that the water of crystallization is separated and evaporated from the gypsum, this water extracted from the gypsum by the paper cylinder 19 by its water absorbing ability evaporates, and, since heat is removed during the evaporation of this water, the surface of the can 2 is cooled. Some of the heat at the top end of the can 2 as well as some of the heat transmitted to the insulation cylinder 17 is able to escape out of the case 21 through the heat vent holes 39 provided in the cover plate 37. The rest of the heat transmitted to the insulation cylinder 17 is conveyed through the paper cylinder 19, the thermal insulation layer 20, the case 21 and the cover 24, in that order, but because most of this heat is intercepted by the thermal insulation layer 20, and also because the portion 25 is corrugated to reduce its area in contact with the user's hand, so that even if the user holds the case 1 with a hand around the portion 25, that hand does not feel hot. The corrugated portion 25 is also useful in preventing the user's hand slipping. Since flat cardboard is used for the portions of the cover 24 on either side of the portion 25, their surfaces can be utilized for printing or pasting operating instructions for the inhaler, or for other purposes. If desired, the entire cover 24 may be corrugated.

The size and weight of the portable oxygen inhaler according to this invention can be selected as appropriate, but in a preferred example thereof, when the device has a capacity for generating oxygen for a period of 15 minutes, it is suggested that the device is designed so that the diameter of the case is 90 mm, the length between the two ends of the case is 250 mm, and the total weight is 800 g.

Thanks to this novel mechanism, the present invention can produce the following advantageous effects.

Because of the use of a chlorate candle which requires only a fraction of the space required for an ordinary oxygen cylinder, this device has a small size and weight, is easy to carry, and is convenient to store. The oxygen can be generated immediately by a very simple operation, that is, by merely pulling on a pull ring, so that anyone can easily use the device. Thus, this device can be kept in any suitable place within reach, such as in the bedroom, toilet, office, car, etc., so that if someone should suddenly have difficulty in breathing during an asthma attack or a heart attack, etc., he can use the device immediately as an emergency oxygen supply until an ambulance or doctor arrives. Since the oxygen is generated by the reaction of a solid core and no pressurized oxygen is used, the oxygen inhaler according to the present invention is safe to carry, handle and store. Moreover, the oxygen inhaler of the present invention, because of its simple construction, requires no inspection throughout the service life of the core and is easy to maintain. Since inexpensive and safe materials are used as the component parts thereof, the oxygen inhaler of the present invention is inexpensive and disposable, and, after disposal it has no ill effects on humans or the environment.

What is claimed is:

1. A portable oxygen inhaler, comprising in combination:
- a stainless steel can,
- a chlorate candle core contained within said can, said core including a solid oxygen-generating agent composed mainly of a chlorate,
- manually actuable ignition means fastened at one end of the can for selectively imparting initial energy to said core to cause a reaction of said core,
- an oxygen outlet and a safety valve located at the other end of said can,
- a soft tube with one end connected to said oxygen outlet,
- normally closed plug means connected to the other end of said tube for automatically opening with a rise in oxygen pressure, a foldable mask of soft material adapted to cover at least one breathing passage of a user, a front opening defined by said mask and having said plug means inserted thereinto, fastening means attached to said mask for securing said mask over the user's face, preventive means coupled to said tube to prevent the accidental bending of said tube to ensure a smooth passage of oxygen therethrough, a thermal insulation cylinder disposed around said can including a cylindrical cardboard cover, a space defined between said cylindrical cardboard cover and the surface of said can, and a solid gypsum filler located in said space, a thermal insulation layer of corrugated cardboard disposed around said cylindrical cardboard cover, a cardboard case located around said thermal insulation layer, said case defining a first space above said can, said insulating cylinder and said insulation layer at said one end of said can for housing said foldable mask and said tube during storage, and a second space below said can, said insulating cylinder and said insulation layer at said other end of said can for housing said ignition means, an open ended cardboard cover sheath extending around said case, the end of said cardboard cover with sheath adjacent to said one end of said can being curled, cardboard end plate means located between said second space and said curled end, an annular block located in said second space and supporting said can, said thermal insulation cylinder and said thermal insulation layer, a first metallic protective cap attached to said end plate means with a peripheral edge of said first cap being held between said block and said end plate means, said first cap serving to prevent any denting of the end plate means by an external force so as to protect said ignition means, a second metallic cap removably covering said first space, tape means for selectively fastening said second cap to an outer surface of said cover sheath, a cardboard cover plate covering said other end of said can, said thermal insulation cylinder and said thermal insulation layer, said cover plate having a center opening encompassing said oxygen outlet and said safety valve, and its periphery being provided with a plurality of heat vent holes, and a paper cylinder located in said first space and engaging said case so as to support said second cap.

* * * * *